(12) United States Patent
Okon

(10) Patent No.: US 11,788,043 B2
(45) Date of Patent: Oct. 17, 2023

(54) CELL CULTURE PLATE, ASSEMBLY AND METHODS OF USE

(71) Applicant: Imoh S. Okon, Duluth, GA (US)

(72) Inventor: Imoh S. Okon, Duluth, GA (US)

(\*) Notice: Subject to any disclaimer, the term of this patent is extended or adjusted under 35 U.S.C. 154(b) by 269 days.

(21) Appl. No.: 16/722,364

(22) Filed: Dec. 20, 2019

(65) Prior Publication Data

US 2020/0199507 A1 Jun. 25, 2020

Related U.S. Application Data

(60) Provisional application No. 62/783,775, filed on Dec. 21, 2018.

(51) Int. Cl.
| | |
|---|---|
| *C12M 1/22* | (2006.01) |
| *C12M 1/00* | (2006.01) |
| *C12M 1/12* | (2006.01) |
| *C12M 1/04* | (2006.01) |

(52) U.S. Cl.
CPC ............ *C12M 23/10* (2013.01); *C12M 23/22* (2013.01); *C12M 23/24* (2013.01); *C12M 25/02* (2013.01); *C12M 47/04* (2013.01)

(58) Field of Classification Search
CPC ....... G02B 21/34; C12M 23/10; C12M 23/22; C12M 23/24; C12M 25/02; C12M 47/04
See application file for complete search history.

(56) References Cited

U.S. PATENT DOCUMENTS

| | | | | |
|---|---|---|---|---|
| 3,432,275 A | * | 3/1969 | Unger ................... | B01L 3/5085 422/552 |
| 4,039,247 A | * | 8/1977 | Lawman ................ | G02B 21/34 359/398 |
| 4,607,921 A | * | 8/1986 | Miller .................... | G02B 21/34 356/246 |
| 4,722,598 A | * | 2/1988 | Ford ....................... | G02B 21/34 356/246 |
| 4,748,124 A | * | 5/1988 | Vogler .................... | C12M 23/34 435/297.1 |
| 4,974,952 A | * | 12/1990 | Focht ..................... | G02B 21/34 359/398 |
| 5,035,494 A | * | 7/1991 | Foldenauer ............. | B29C 66/54 359/536 |
| 5,044,500 A | * | 9/1991 | Webber .................. | G02B 21/34 206/456 |
| 5,170,286 A | * | 12/1992 | Zimmerberg .......... | G02B 21/34 359/398 |
| 5,430,542 A | * | 7/1995 | Shepherd ............... | G01N 21/05 356/246 |
| 9,005,550 B2 | | 4/2015 | Carter et al. | |
| 9,040,293 B2 | | 5/2015 | Gulzow et al. | |
| 9,128,300 B2 | | 9/2015 | McLellan et al. | |

(Continued)

OTHER PUBLICATIONS

Rhodes, et al., A Novel Hinge System and Incubation Chamber for Emulsion-coated Coverslip Autoradiography, The Journal of Histochemistry and Cytochemistry vol. 41, No. 9, pp. 1419-1427 (Year: 1993).*

(Continued)

*Primary Examiner* — William H. Beisner
*Assistant Examiner* — Danielle B Henkel
(74) *Attorney, Agent, or Firm* — BALLARD SPAHR LLP

(57) ABSTRACT

A cell culture system or assembly, flask, plate and dish for growing, viewing and evaluating cells; and methods of use.

6 Claims, 16 Drawing Sheets

(56) References Cited

U.S. PATENT DOCUMENTS

| | | | |
|---|---|---|---|
| 2004/0091393 A1* | 5/2004 | Richardson | B01L 3/508 422/400 |
| 2005/0170522 A1* | 8/2005 | Samsoondar | B01L 3/508 436/169 |
| 2007/0128069 A1* | 6/2007 | Louis | B29C 66/727 422/400 |
| 2010/0221768 A1 | 9/2010 | Akai et al. | |
| 2012/0015431 A1 | 1/2012 | Niehren | |
| 2013/0344579 A1 | 12/2013 | Izapy et al. | |
| 2015/0218503 A1 | 8/2015 | Klyama et al. | |
| 2016/0002585 A1 | 1/2016 | Reid et al. | |
| 2016/0274008 A1 | 9/2016 | Chen et al. | |

OTHER PUBLICATIONS

U.S. Appl. No. 62/783,775, filed Dec. 20, 2019, Imoh S. Okon.

* cited by examiner

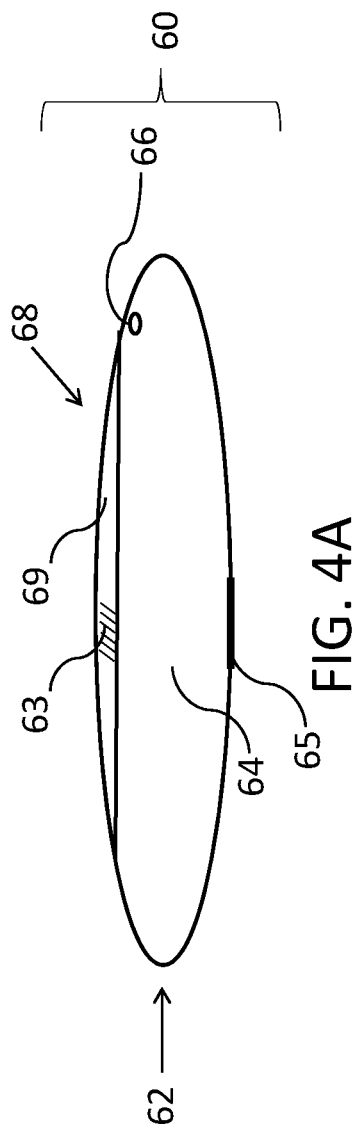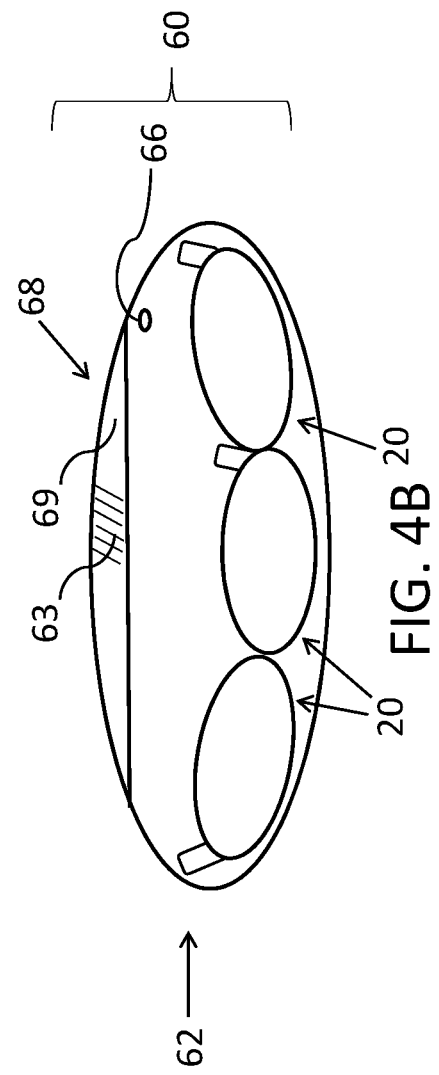

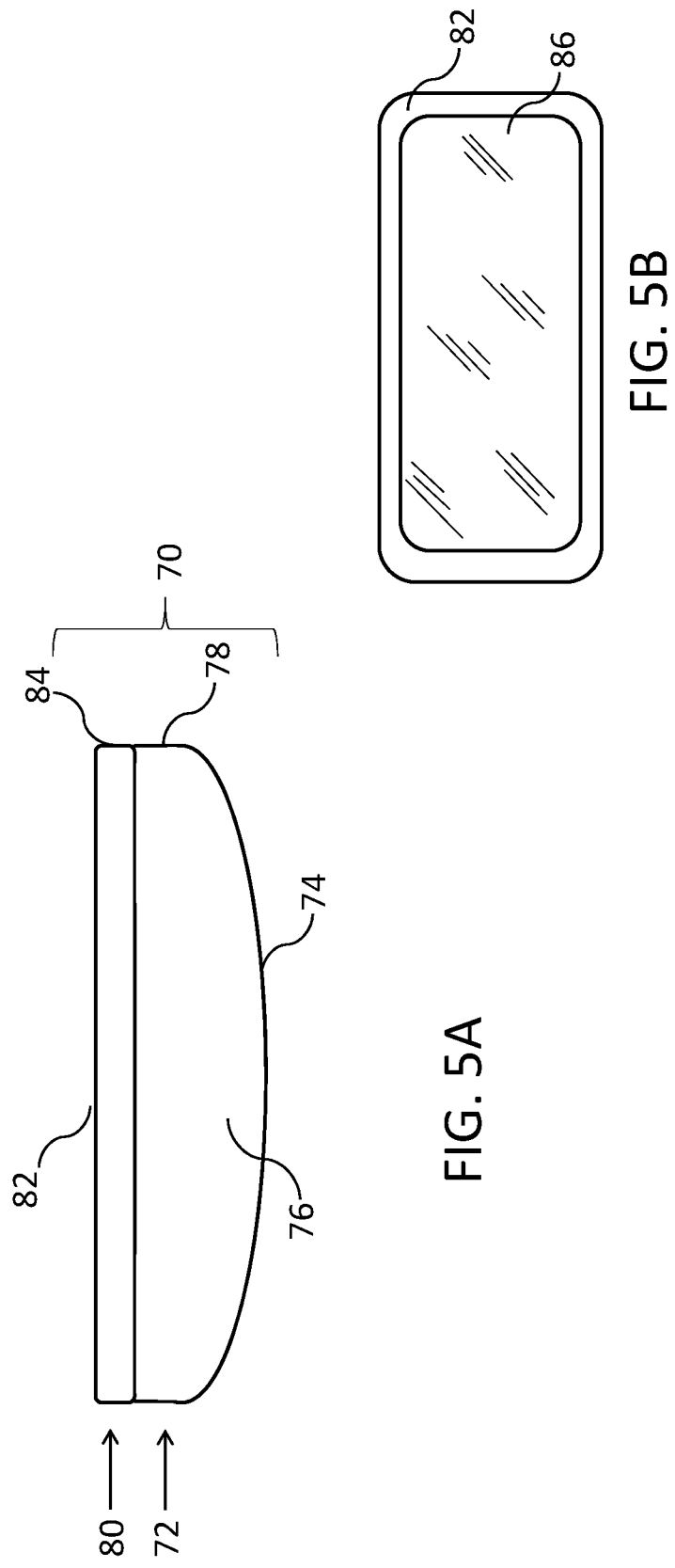

CELL CULTURE PLATE, ASSEMBLY AND METHODS OF USE

CROSS-REFERENCE TO RELATED PATENT APPLICATIONS

This application is based upon and claims priority to U.S. Provisional Application No. 62/783,775 filed on Dec. 21, 2018, and is hereby incorporated herein by reference.

FIELD OF INVENTION

The present disclosure relates to cell culture plates, flasks and assemblies for growing and viewing cells, cell cultures; and methods of use.

BACKGROUND

Cell cultures provide for the growth and maintenance of a cell or cells in a variety of conditions for varying types of analyses including examining the resulting growth under a microscope. Using conventional devices and kits can be inadequate under certain conditions. A common problem is removing the cells from the original culturing platform to a slide for visual evaluation without breaking the slide or contaminating the cells. A need exists for a slide, plate or system that allows analysis including microscopy of the cultured cells while maintaining the integrity of the cultured cells.

SUMMARY

Described herein, in one aspect, is a cell culture assembly for holding one or more cells, the assembly comprising: a slide comprising: a top surface; a bottom surface; at least one edge; and at least one projection attached to said edge; and a cover slip comprising: a top surface; a bottom surface; and at least one aperture to accommodate said at least one projection; wherein said cover slip overlaps with at least a portion of said slide; and wherein said cover slip is transparent.

Disclosed herein, in one aspect, is a cell culture assembly for holding one or more cells, the assembly comprising: a slide comprising: a top surface; a bottom surface; and at least one edge; a cover slip comprising: a top surface; a bottom surface; and at least one edge; wherein said cover slip is transparent; and a hinge connecting said slide and said cover slip.

Disclosed herein, in one aspect, is a cell culture flask for culturing one or more cells, the cell culture flask comprising: a container comprising: a top surface; a bottom surface; at least one sidewall; at least one port; and at least one vent; wherein said top surface is transparent and comprises a magnifying region.

Disclosed herein, in one aspect, is a cell culture plate for culturing one or more cells, the cell culture plate comprising: a container comprising: an internal cavity; and a vent; and a lid comprising: a top surface, wherein the top surface of the lid comprises a grip portion.

Disclosed herein, in one aspect, is a cell culture dish comprising: a base comprising: a bottom portion; an internal cavity; and a sidewall portion extending upward therefrom; and a lid comprising: a top portion comprising a magnifying region; and a wall portion; wherein the lid is adapted to cover the base; and wherein the wall portion extends downward therefrom.

Disclosed herein, in one aspect, is a cell culture assembly comprising: a top chamber comprising: an internal cavity; and a port; a bottom chamber comprising: an internal cavity; and a port; and a semi-permeable vessel comprising: a top membrane; a bottom membrane; at least one port; and wherein the semi-permeable vessel is positioned between the top chamber and bottom chamber and wherein the semi-permeable vessel is configured to fluidly interconnect the top and bottom chamber.

Disclosed herein, in one aspect, is a cell culture assembly comprising: a chamber comprising: an internal cavity; and a port; and a semi-permeable vessel comprising: a membrane; and at least one port; and wherein the semi-permeable vessel overlays the chamber and wherein the semi-permeable vessel is configured to fluidly interconnect with the chamber.

Disclosed herein, in one aspect, is a cell culture assembly for holding one or more cells, the assembly comprising: a cover slip comprising: a top surface; a bottom surface; at least one edge; and at least one projection attached to said edge; and a slide comprising: a top surface; a bottom surface; and at least one aperture to accommodate said at least one projection; wherein said cover slip overlaps with at least a portion of said slide; and wherein said cover slip is transparent.

BRIEF DESCRIPTION OF THE DRAWINGS

The drawings herein illustrate embodiments and together with the description, serve to explain the principles of the cell culture plates, flasks, assemblies and method:

FIG. 4A is a side perspective view of an aspect of a cell culture plate according the present disclosure.

FIG. 4B is a side perspective view of another aspect of a cell culture plate according the present disclosure.

FIG. 5A is a side perspective view of an aspect of a cell culture dish according to the present disclosure.

FIG. 5B is a top perspective view of the magnifying region of the cell culture dish according to the present disclosure.

DETAILED DESCRIPTION

Before the present cell culture tools, assembly and methods are disclosed and described, it is to be understood that the cell culture tools, assembly and methods are not limited to specific methods, specific components, or to particular implementations. Like numbers refer to like elements throughout. It is also to be understood that the terminology used herein is for the purpose of describing particular embodiments and is not intended to be limiting.

Many modifications and other embodiments of the disclosure set forth herein will come to mind to one skilled in the art to which the invention pertains having the benefit of the teachings presented in the foregoing description and the associated drawings. Therefore, it is to be understood that the disclosure is not to be limited to the specific embodiments described herein and that modifications and other embodiments are intended to be included within the scope of the appended claims. Although specific terms are employed herein, they are used in a generic and descriptive sense only and not for purposes of limitation.

As used herein, the singular forms "a," "an" and "the" include plural referents unless the context clearly dictates otherwise.

The word "or" as used herein means any one member of a particular list and also includes any combination of members of that list.

As used herein, the terms "optional" or "optionally" mean that the subsequently described event, feature or circumstance may or may not occur, and that the description includes instances where said event, feature or circumstance occurs and instances where it does not.

As used in the specification and in the claims, the term "comprising" can include the aspects "consisting of" and "consisting essentially of." "Comprising" can also mean "including but not limited to."

The phrase "such as" is not used in a restrictive sense, but for explanatory purposes.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Figure 8:
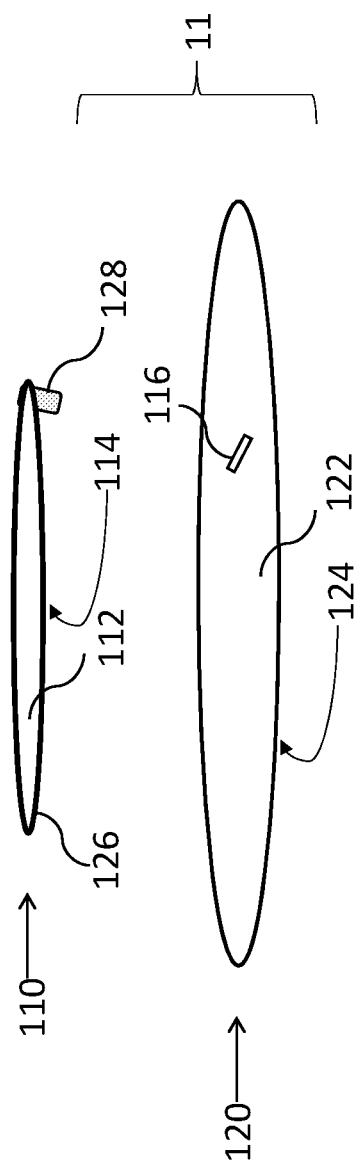
FIG. 8 is a side perspective views of one aspect of a cell culture assembly according to the present disclosure.

Disclosed herein, with reference to FIGS. 1-2 and 8, a cell culture assembly 1, a cell culture assembly 3, and a cell culture assembly 11 useful for holding one more cells are illustrated. Cell culture assemblies 1, 3 and 11 improve the means for removing cells from a growth medium for subsequent analysis. As described herein, cell culture assembly 1 (see, FIG. 1) and cell culture assembly 11 (see, FIG. 8) can hold one more cells for analysis under a microscope. Cell culture assembly 1 permits the removal of slide 20, from, for example, a culture media, containing one or more cells to be easily covered with cover slip 10. In another embodiment, cell culture assembly 11 permits the removal of slide 120, from, for example, a culture media, containing one or more cells to be easily covered with cover slip 110. Alternatively, cell culture assembly 3 (see, FIG. 2) allows the removal of both cover slip 30 together with slide 40 from, for example, a culture media, containing one or more cells that can then be easily covered with the cover slip 30 that is connected to slide 40 via a hinge 38.

Figure 1A:
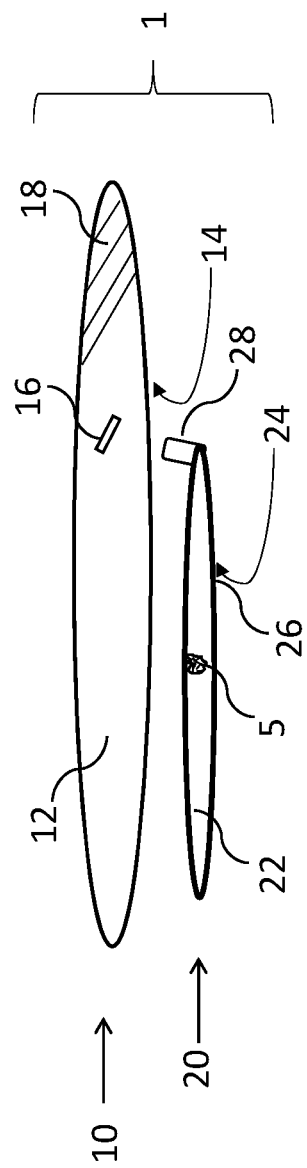
FIGS. 1A-B are side perspective views of one aspect of a cell culture assembly according to the present disclosure.

As shown in FIG. 1A, cell culture assembly 1 comprises a cover slip 10 and a slide 20. Referencing FIG. 1A, cover slip 10 comprises a top surface 12, a bottom surface 14 and at least one aperture 16. In some aspects, cover slip 10 can be configured with at least one aperture 16 for accommodating the at least one projection 28 of slide 20.

As shown in FIG. 8, cell culture assembly 11 comprises a cover slip 110 and a slide 120. Referencing FIG. 8, cover slip 110 comprises a top surface 112, a bottom surface 114 and at least one projection 128. In some aspects, slide 120 can be configured with at least one aperture 116 for accommodating the at least one projection 128 of cover slip 110.

Figure 1B:
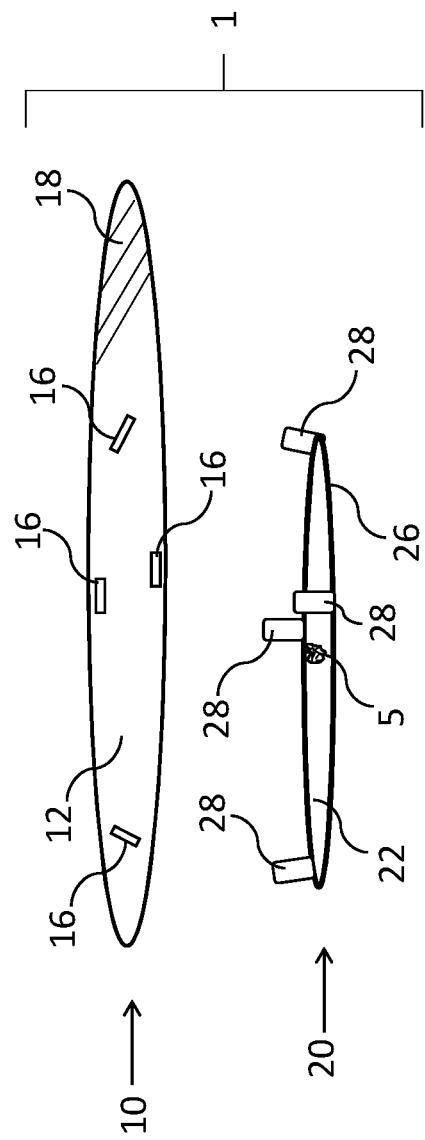

Referring to FIG. 1B, the number of apertures 16 positioned on cover slip 10 can depend on the number of projections 28. Generally, for cell culture assemblies 1 and 11, the number of apertures 16 or 116 positioned on cover slip 10 or slide 120, respectively can depend on the number of projections 28 or 128. For example, the number of apertures 16 or 116 can be at least 1, 2, 3, 4, or more. The number of projections 28 or 128 of slide 20 or cover slip 110, respectively, can be at least 1, 2, 3, 4, or more. In some aspects, slide 20 can be configured to comprise two or more projections 28 substantially equally spaced. In some aspects, cover slip 110 can be configured to comprise two or more projections 128 substantially equally spaced. In some aspects, any of the at least one apertures 16 and 116 described herein can be designed to complementarily receive, for example, the at least one projection 28 and 128. The diameter of aperture 16 and 116 can be sufficient to receive the at least one projection 28 and 128. The at least one aperture 16 and 116, for example, can be of sufficient length and width to accommodate projection 28 and 128. In some aspects, the at least one projection 28 and 128 can be self-locking in said aperture 16 and 116. In some aspects, aperture 16 and 116 can have a width of 0.2 cm to 0.5 cm and a length of 0.5 cm to 1.0 cm, or any combination thereof. In some aspects, aperture 16 and 116 can be of any shape, width or length. In some aspects, aperture 16 and 116 can be square, rectangular or round.

The top surface 12 of cover slip 10 can further comprise a labeling region 18. In some aspects, the labeling region 18 can be a bar code. Labeling region 18 can be positioned anywhere on the top surface 12 of cover slip 10. In some aspects, labeling region 18 provides an identification zone for marking the cover slip 10. In some aspects, labeling region 18 can visually contrast with the non-labeled region of the top surface 12 of the cover slip 10. Labeling region 18 can cover various amounts of surface of area. For example, labeling region 18 can cover a surface area of at least 30% or less of the top surface 12 of cover slip 10. As shown in FIG. 1, labeling region 18 can be positioned toward one side of the top surface 12 of cover slip 10. Typically, the labeling region 18 can be constructed of a variety of materials in a number of ways. Generally, the labeling region 18 can comprise a coating. A coating in this context means a composition which solidified on application to the top surface 12 of cover slip 10. The coating may be applied on the top surface 12 of cover slip 10 by conventional means. It may involve cross-linking or polymerization of a carrier and/or loss of a solvent. The carrier can include polyurethane, polyvinyl butyral, polyester resins, polyamides, polyimides, epoxy resins, epoxy/vinyl/polyester coatings and lacquers, polyvinylalcohol, polyvinyl acetate, acetal and siloxane resins. In some aspects, the carrier can be polyurethane or an epoxy resin. The coating and the labeling region 18 can be resistant to laboratory solvents, reagents, stains and chemicals, which may remove, blur or obscure important information on the top surface 12 of cover slip 10. The carrier can generally be dissolved or dispersed in a solvent. Suitable solvents include those that are commonly used for inks and lacquers, such as water, ethanol, ethyl acetate, isopropyl alcohol and lower hydrocarbons.

As shown in FIG. 1A and FIG. 8, cover slip 10 and 110 can be flat and transparent. Cover slip 10 and 110 can be transparent to relevant light (usually visible). Examples of visible light include but are not limited to X-rays, gamma rays, ultraviolet light, infrared light, radio waves and visible light. In some aspects, the cover slip 10 and 110 can be made in its entirety of a transparent plastic or glass. In some aspects, cover slip 10 and 110 can be optically transparent. Cover slip 10 and 110 can be made of suitable material that does not react with other materials to which it is applied. Cover slip 10 and 110 can be rigid such that it can be manipulated by hand or robot. In some aspects, cover slip 10 and 110 can be of a uniform thickness throughout.

Figure 1C:
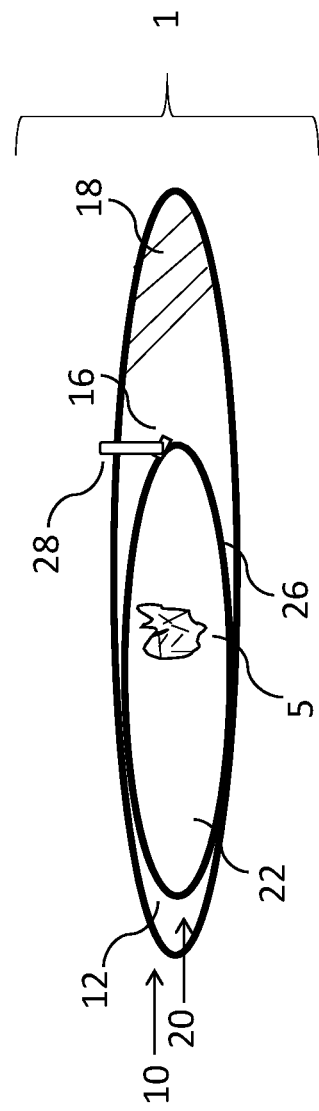
FIG. 1C shows one aspect of a cell culture assembly in the closed position according to the present disclosure.

In some aspects, cover slip 10 and 110 can generally be a thin, flat strip of glass, and can be of any shape. For example, cover slip 10 and 110 can have a round, oval or elliptical shape. In some aspects, clover slip 10 and 110 can be in a rectangle shape. Cover slip 10, when placed over slide 20, can overlap with at least a portion of slide 20. As shown in FIGS. 1A-C, cover slip 10 can be used with slide 20 forming cell culture assembly 1. Cover slip 10, when secured to slide 20, can provide an airtight seal around a specimen (e.g., one or more cells) or sample 5 contained therein. In some aspects, the at least one aperture 16 can be positioned such that it can be offset from the center of cover slip 10. Similarly, as shown in FIG. 8, cover slip 110 can be used with slide 120 forming cell culture assembly 11. Cover slip 110, when secured to slide 120, can provide an airtight seal around a specimen (e.g., one or more cells) or sample 5 contained therein. In some aspects, the at least one aperture 116 can be positioned such that it can be offset from the center of slide 110.

Referencing FIG. 1A, slide 20 can comprise a top surface 22, a bottom surface 24, at least one edge 26 and at least one projection 28. The at least one projection 28 can be attached to the at least one edge 26 and extend upwardly from slide 20. The projection 28 can be rigid such that it can be manipulated by hand. In some aspects, the at least one aperture 16 of cover slip 10 can receive the at least one projection 28 of slide 20. For example, the at least one aperture 16 of cover slip 10 can be adapted to accommodate the at least one projection 28 of slide 20 for securing the bottom surface 14 of cover slip 10 to the top surface 22 of slide 20. Edge 26 can be linear, non-linear or a single continuous linear or non-linear edge.

Referencing FIG. 8, slide 120 can comprise a top surface 122, a bottom surface 124, and at least one aperture 116. Cover slip 110 can comprise a top surface 112, a bottom surface 114, at least one edge 126 and at least one projection 128. The at least one projection 128 can be attached to the at least one edge 126 and extend downwardly from cover slip 110. The projection 128 can be rigid such that it can be manipulated by hand. In some aspects, the at least one aperture 116 of slide 120 can receive the at least one projection 128 of cover slip 110. For example, the at least one aperture 116 of slide 120 can be adapted to accommodate the at least one projection 128 of cover slip 110 for securing the bottom surface 114 of cover slip 110 to the top surface 122 of slide 120. Edge 126 can be linear, non-linear or a single continuous linear or non-linear edge.

Referencing FIG. 1B, slide 20 can comprise a top surface 22, a bottom surface 24, at least one edge 26 and at least one projection 28. Two or more projections 28 can be attached to the at least one edge 26 and extend upwardly from slide 20. The projections 28 can be rigid such that they can be manipulated by hand. In some aspects, two or more apertures 16 of cover slip 10 can receive two or more projections 28 of slide 20. For example, two or more apertures 16 of cover slip 10 can be adapted to accommodate two or more projections 28 of slide 20 for securing the bottom surface 14 of cover slip 10 to the top surface 22 of slide 20. Edge 26 can be linear, non-linear or a single continuous linear or non-linear edge.

As shown in FIGS. 1A-C and FIG. 8, slide 20 and 120 can be flat and transparent. Slide 20 and 120 can be transparent to relevant light (usually visible). In some aspects, slide 20 or slide 120 can be made in its entirety of a transparent plastic or glass. Slide 20 and 120 can be made of suitable material that does not react with other materials to which it is applied. Slide 20 and 120 can be rigid such that it can be manipulated by hand or robot. In some aspects, slide 20 and 120 can be of a uniform thickness throughout.

In some aspects, slide 20 and 120 can generally be a thin, flat strip of glass, and can be of any shape. In some aspects, slide 20 and 120 can have a round, oval, circular or elipitic shape. In some aspects, slide 20 and 120 can be the same or a different shape than cover slip 10 and 110. In some aspects, slide 20 and 120 can have a smaller perimeter, circumference or area as compared to cover slip 10 and 110. In some aspects, slide 20 and 120 can have a larger perimeter, circumference or area as compared to cover slip 10 and 110. The holding capacity of slide 20 or slide 120 can be in the range of 0.1 ml (100 µl) to 1 ml (1000 µl). A dimension of slide 20 or slide 120 can be sufficient to be accommodated, and be substantially held in position, by a standard mechanical stage specimen holder of a microscope. For instance, the diameter of slide 20 and 120 can be between 12 mm and 25 mm. In some aspects, the diameter of slide 20 and 120 can be between 10 mm and 32 mm or any number in between. In some aspects, the diameter of slide 20 and 120 can be 12 mm, 15 mm, 18 mm, 22 mm, 25 mm or 32 mm. The overall size of slide 20 and 120 including its diameter should be such that the slide 20 is of a sufficient size to be placed in a multi-well plate. In some aspects, slide 20 should be of a sufficient size that when in the closed position with cover slip 10, cell culture assembly 1 can be placed in a multi-well plate. In some aspects, slide 120 should be of a sufficient size that when in the closed position with cover slip 110, cell culture assembly 11 can be placed in a multi-well plate. Slide 20 and 120 can also be made from any sturdy material such as plastic.

Suitable plastic materials include but are not limited to transparent plastic materials like polystyrene, polypropylene, polymethylpentene, polycarbonate, polymethylmethacrylate, polymethylacrylmethylimide, cycloolefine copolymer, and UV-transmittable acrylic resin as well as of mixtures and/or copolymers of at least two of these plastic materials. The same material or different material can make up the cover slip 10 (and 110) and slide 20 (and 120), as well as cover slip 30 and slide 40. A transparent plastic material permits optical examination of one or more cells. In some aspects, cell culture assemblies 1, 3 and 11 can be entirely or partly made of plastic material that is as clear as glass.

Suitable glass materials include but are not limited to soda lime glass, borosilicate glass or transparent plastic. Suitable transparent plastics are crystal-clear polystyrene or UV-transmittable acrylic resin. In some aspects, cell culture assembly 1 and cell culture assembly 3 can be entirely or partly made of glass material.

In some aspects, slides 20, 40 and 120, and cover slips 10, 30 and 110 can be constructed from a chemical that can be made of a heat resistant material. In some aspects, the cover slips 10, 30 and 110 can further comprise an adhesive applied on the bottom surface 14, 34 and 114, respectively, capable of bonding the top surface 22, 42 and 122 of said slide 20, 40 and 120 to the cover slip 10, 30 and 110, respectively. In some aspects, cover slips 10, 30 and 110 can further comprise an adhesive applied to the bottom surface 14 and 34 and 114 capable of bonding top surface 22, 42 and 124 of said slide 20, 40, 120 to the cover slip 10, 30 and 110, respectively. In this embodiment, top surface 22, 42 or 122 of slide 20, 40 or 120 can be positioned or come into contact with the bottom surface 14, 34 and 114 of cover slip 10, 30 and 110, respectively. The configuration of slide 20, 40 and 120 with cover slip 10, 30 and 110 can depend on whether an objective microscope or an inverted microscope is used for observation.

In some aspects, slides 20, 40 and/or 120, and cover slips 10, 30 and 110 can be sterile or sterilized. In some aspects, cell culture assemblies 1, 3, 90 and/or 100 can be sterile or sterilized.

Figure 5C:
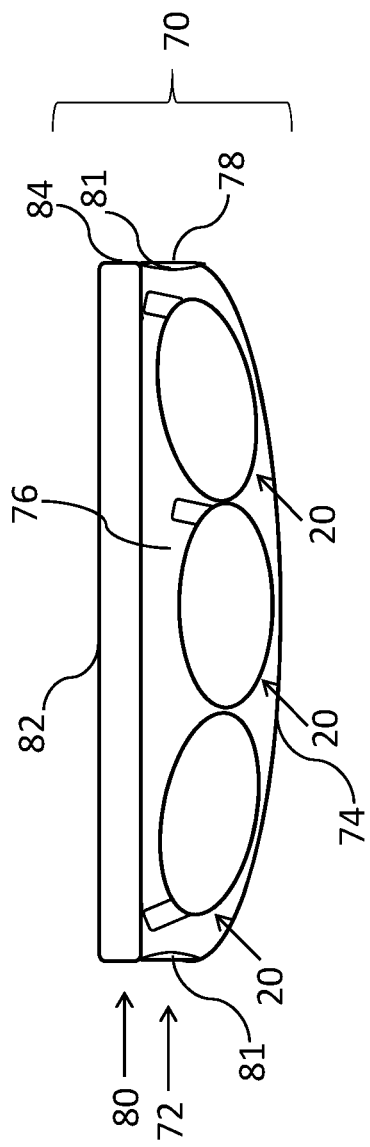
FIG. 5C is a side perspective of view of another aspect of a cell culture dish according to the present disclosure.
Figure 6A:
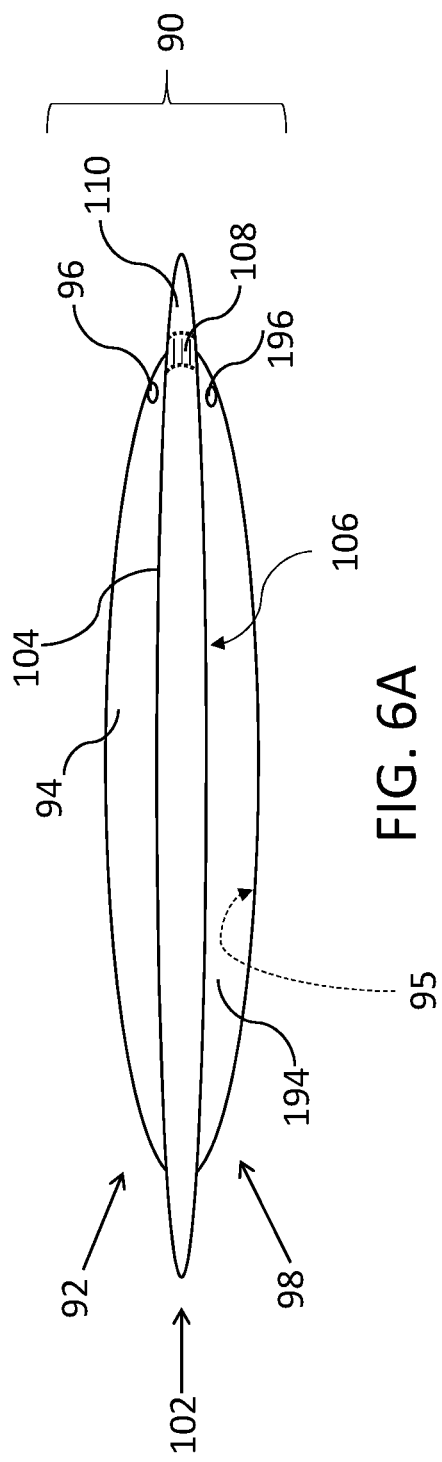
FIGS. 6A-B show side perspective views of other aspects of a cell culture assembly according to the present disclosure
Figure 6B:
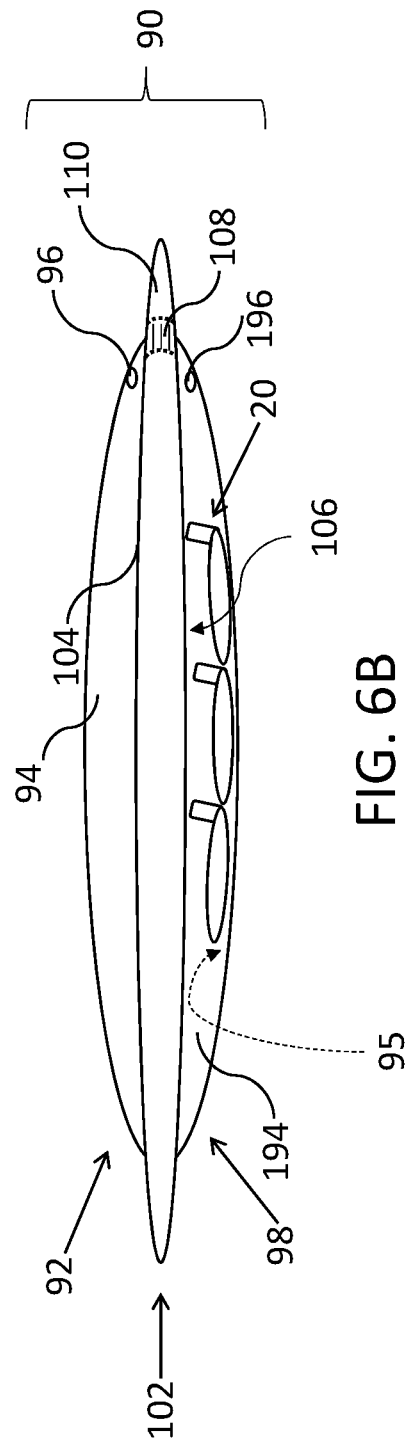

In use, slide 20 (and slide 120) can be placed in a cell culture plate 60, cell culture dish 70 or cell culture assembly 90 as shown, for example, in FIGS. 4B, 5C and 6B, respectively. Specimens (e.g., one or more cells) or a sample 5 can be placed and grown on the top surface 22 or 122 of slide 20 or 120, respectively. In some aspects, slide 20 and 120 can be sterilized prior to use. Cell culture plate 60, petri dish 70 or cell culture assembly 90 can hold, for example, multiple slides 20 and 120 or a combination thereof. To assess the growth of the cells on slide 20, cover slip 10 can be placed in a number of positions over slide 20, serving to cover a sample 5 (e.g., one or more cells). Similarly, cover slip 110 can be placed over slide 120 to form assembly 11 such that the cells present on slide 120 can be further analyzed. In some aspects, cover slip 10 and 110 can be sterilized prior to use. For removing slide 20 from, for example, a cell culture plate 60, a petri dish 70 or a cell culture assembly 90, a user can grip projection 28 using his/her thumb and forefinger. Such configuration permits the easy removal of the slide 20 from, for example, a petri dish 70 while the projection 28 can serve to connect slide 20 to cover slip 10. Next, cover slip 10 and 110 can be secured to slide 20 and 120, respectively, by positioning the at least one projection 28 and 128 through the at least one aperture 16 and 116. Thus, the risk of contamination of one or more of the cells when arranging the cover slip 10 (and 110) over slide 20 (and 120) and securing the cell culture assembly 1 (and 11) can be reduced.

FIG. 1C shows cell culture assembly 1 in a fully closed position such that the sample 5 can be completely covered by the cover slip 10 and can therefore be wholly contained within cell culture assembly 1. For this, bottom surface 14 (not shown) of cover slip 10 can be in contact with the top surface 22 of slide 20 as shown in FIG. 1A, forming cell culture assembly 1. Cell culture assembly 1 can then be placed under a microscope for further analysis. For example, bottom surface 24 of slide 20 generally faces the optics of a microscope when inserted therein. As shown in FIG. 1C, cover slip 10 extends over entire slide 20. Variations in cover slip 10 shape, number of apertures 16 as well as variations in slide 20 shape and number of corresponding projections 28 are within the scope of the invention.

Figure 2A:
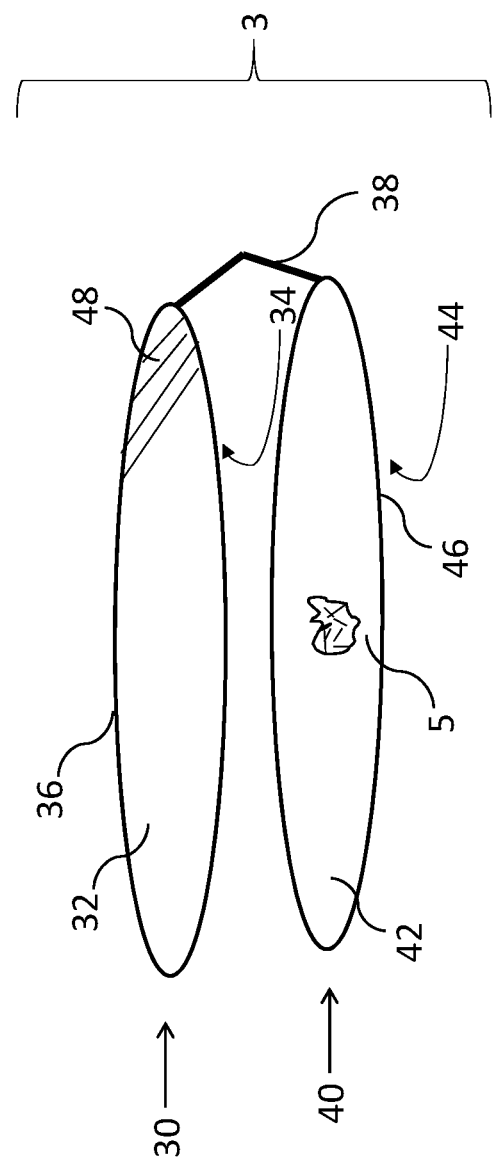
FIG. 2A is a side perspective view of another aspect of a cell culture assembly according to the present disclosure.
Figure 2B:
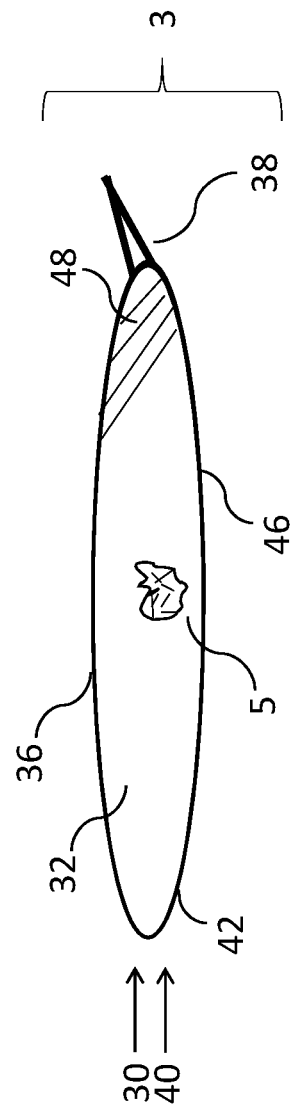
FIG. 2B shows one aspect of a cell culture assembly in the closed position according to the present disclosure.
Figure 2C:
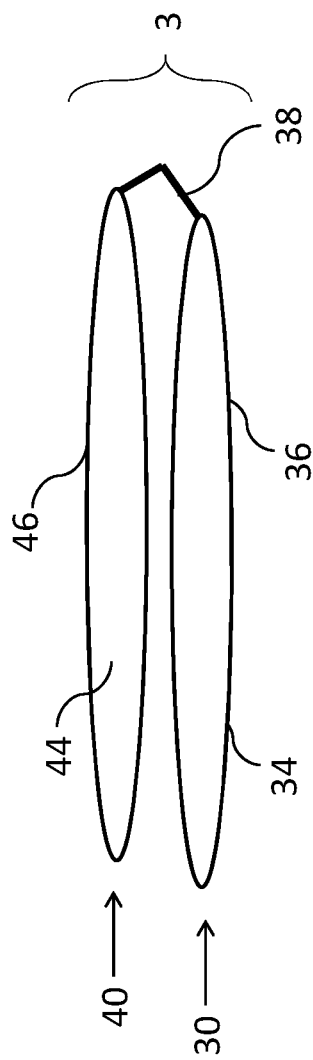
FIG. 2C is a side perspective view of another aspect of a cell culture assembly according to the present disclosure.

As shown in FIGS. 2A-C, a cell culture assembly 3 for holding one or more cells can comprise a slide 40 and a cover slip 30. Referencing FIGS. 2A and 2C, slide 40 can comprise a top surface 42, a bottom surface 44 and at least one edge 46. As shown in FIGS. 2A and 2C, cover slip 30 can comprise a top surface 32, a bottom surface 34 and at least one edge 36. Cover slip 30 can be transparent and optically clear. Cell culture assembly 3 can also comprise a hinge 38 connecting slide 40 to cover slip 30. Hinge 38 serves to position and secure cover slip 30 over slide 40. Edge 46 can be linear, non-linear or a single continuous linear or non-linear edge.

As shown in FIGS. 2A-C, slide 40 and cover slip 30 can be flat and transparent. Slide 40 and cover slip 30 can be transparent to relevant light (usually visible). Slide 40 and cover slip 30 can be made in their entirety of a transparent plastic or glass. In some aspects, cover slip 30 can be optically transparent. Slide 40 can be made of suitable material that does not react with other materials to which it is applied. Cell culture assembly 3 can be rigid such that it can be manipulated by hand or robot. In some aspects, slide 40 and cover slip 30 can be of a uniform thickness throughout.

Slide 40 and cover slip 30 can generally be a thin, flat strip of glass or plastic, and can be of any shape. In some aspects, slide 40 can have a round, oval, circular or elliptical shape. In some aspects, cover slip 30 can have a round, oval, circular or elliptical shape. Generally, the slide 40 can be the same shape as cover slip 30. In some aspects, slide 40 can have a smaller perimeter, circumference or area as compared to coverslip 30. The holding capacity of slide 40 can be in the range of 0.1 ml (100 μl) to 1 ml (1000 μl). The dimensions of cell culture assembly 3 can be sufficient to be accommodated, and be substantially held in position, by a standard mechanical stage specimen holder of a microscope. For instance, the diameter of slide 40 can be about 12 mm to 25 mm. In some aspects, the diameter of slide 40 can be 12 mm, 15 mm, 18 mm, 22 mm or 25 mm. The diameter of cover slip 30 can be about 15 mm to 28 mm. In some aspects, the diameter of cover slip 30 can be 15 mm, 18 mm, 21 mm, 24 mm or 28 mm. Slide 40 and cover slip 30 can also be made from any sturdy material such as plastic.

As shown in FIGS. 2A-C, a hinge 38 can connect slide 40 and cover slip 30 at their respective edges (e.g., 36 and 46). Hinge 38 can extend from slide 40 to cover slip 30. Hinge 38 can be made of flexible or elastic material connecting two relatively inflexible end portions to take up two stable positions (e.g., open and closed). For example, hinge 38 can connect slide 40 and cover slip 30 such that the slide 40 and cover slip 30 can be mounted facing each other with the middle point of each lying toward the other when the cell assembly 3 is in the closed position (see, FIG. 2B). Hinge 38 can be of any elastic material. Hinge 38 can be made from any sturdy material, including plastic. In some aspects, hinge 38 can be molded or bonded to the at least one edge (e.g., 46 and 36, respectively) of slide 40 and cover slip 30. In some aspects, hinge 38 can be made of a plastic material referred to as acetal. Hinge 38 can be of sufficient strength to remain in the closed position once cover slip 30 is placed over slide 40.

In use, cell culture assembly 3 can be placed in a cell culture plate 60 or cell culture dish 70. Cell culture assembly 3 can also be placed in a commercially available cell culture plate or dish. Specimens (e.g., one or more cells) or a sample 5 can be placed and grown on top surface 42 of slide 40. Cell culture assembly 3 can be sterilized prior to use. Cell culture plate 60, petri dish 70 or cell culture assembly 90 can hold, for example, multiple cell culture assemblies 3. To assess the growth of the cells on slide 40, cover slip 30 can be placed over slide 40, serving to cover a sample 5 (e.g., one or more cells). For removing a cell culture assembly 3 from, for example, a cell culture plate 60 or a cell culture dish 70, a user can grip the outer portion of the cover slip 30 (or hinge 38) using a pair of forceps, tweezers, pincers or his/her thumb and forefinger. Next, cover slip 30 can be secured to slide 40 by applying light pressure to cover slip 30 such that the top surface 42 faces the bottom surface 34 of cover slip 30. Thus, the risk of contamination of one or more of the cells when arranging cover slip 30 over slide 40 and securing the cell culture assembly 3 is reduced.

FIG. 2B, shows the cell culture assembly 3 in a fully closed position such that sample 5 can be completely covered by cover slip 30 and can therefore be wholly contained within the cell culture assembly 3. For this, bottom surface 34 (not shown) of cover slip 30 can be in contact with the top surface 42 of slide 40 as shown in FIG. 2B forming cell culture assembly 3. Cell culture assembly 3 can then be placed under a microscope for further analysis. For example, bottom surface 44 of slide 40 generally faces the optics of a microscope when inserted therein. As shown in FIG. 2B, cover slip 30 extends over the entire slide 40. Variations in cover slip 30 shape as well as variations in slide 40 shape are within the scope of the invention.

As noted above, cell culture assemblies 1 and 3 can be used in combination with cell culture plate 60, cell culture dish 70, or cell culture assemblies 90 or 100. Alternatively, cell culture assemblies 1 and 3 can be used in combination with commercially available 6, 12 or 24 well cell culture plates.

Disclosed herein, with reference to FIGS. 3-5, are containers or units useful for culturing one or more cells. Cell culture flask 50 improves the means for culturing cells and assessing the growth of the cells inside the flask 50 without removing the cells from flask 50 or transporting the flask 50 to a microscope. Cell culture plate 60 permits the culturing of cells. In some aspects, cell culture plate 60 permits the culturing of cells while accommodating one or more slides 20 and/or 40 described herein. Cell culture plate 60 can also be used with commercially available slides. While the cells can be assessed directly through the transparent lid 68, slides 20 and 40 can be easily removed from container 62 and covered with cover slips 10 and 30, respectively, for further assessment under a microscope thereby reducing the loss of cells through either dropping or breaking a conventional slide; and reducing contamination to both the user and the cultured cells.

As shown in FIG. 3, cell culture flask 50 for culturing one or more cells comprises a container 52. Container 52 can comprise a top surface 54, a bottom surface 56, at least one sidewall 58, at least one port 57, and at least one vent 53. In some aspects, container 52 can have a plurality of vents 53. The number of vents 53 can be at least 1, 2, 3, 4, or more. One or more vents 53 can be placed anywhere on container 52. In some aspects, container 52 can have at least two vents 53. Generally, container 52 can be rectangular in shape. Alternatively, container 52 can have a spherical shape. To avoid or minimize leaks, container 52 can be blow molded from a single piece of plastic. Examples of plastic that can be used include but are not limited to polyethylene terephthalate with a glycol additive. In some aspects, container 52 can be formed of a clear, sterilizable and wettable resin. The resin can be an alkylene glycol polyester or a polyethylene glycol terephthalate polymer. Sidewall 58 can be flat as shown in FIG. 3A. Bottom surface 56 can slant out as shown in FIG. 3A. In some aspects, bottom surface 56 can be concave.

Figure 3A:
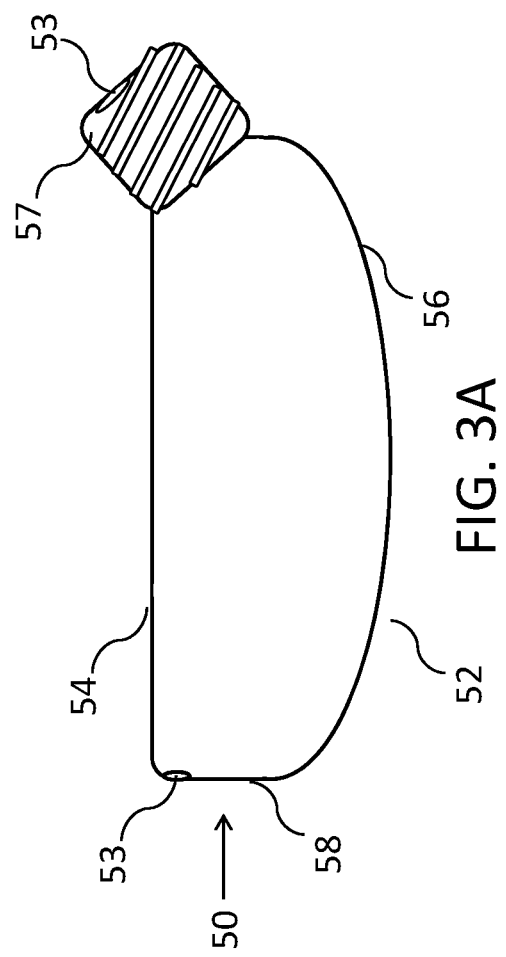
FIG. 3A is a side perspective view of one aspect of a cell culture flask according to the present disclosure.
Figure 3C:
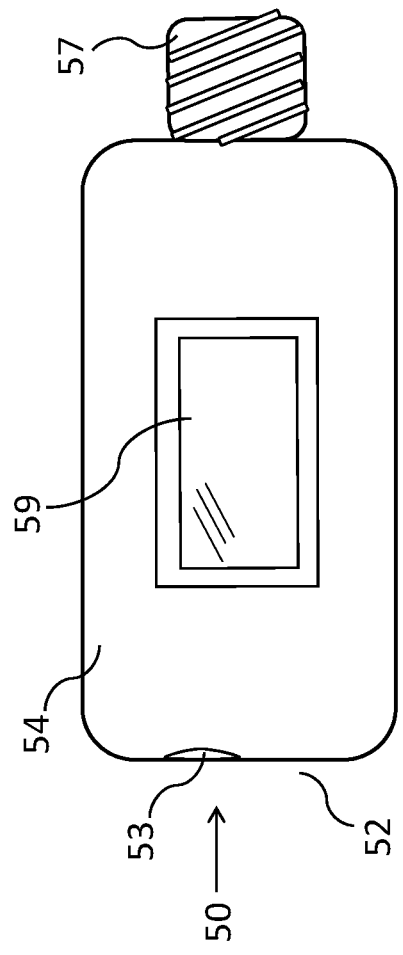
FIG. 3C is a top perspective view of another aspect of the cell culture flask according to the present disclosure.
Figure 3D:
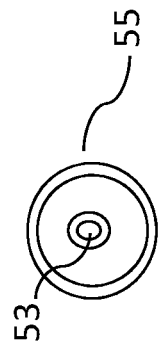
FIG. 3D is a top perspective view showing the cap of the cell culture flask according to the present disclosure.
Figure 3B:
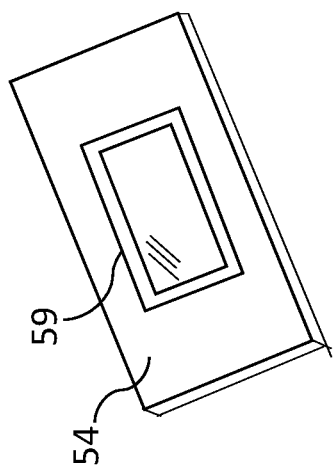
FIG. 3B is an enlarged view of an embodiment showing the magnifying region of a cell culture flask according to the present disclosure.

Referring to FIG. 3A, cell culture flask 50 can have a mixture of flat and bowed areas. Cell culture flask 50 can have any shape desirable. In some aspects, the top surface 54 can be flat. Top surface 54 can be transparent and can be formed of a transparent material. The transparent material can be plastic or a tempered glass. Examples of plastic include but are not limited to lexan or acryl. In some aspects, top surface 54 can have a convex sloped configuration. Regardless of the shape or configuration of the top surface 54, the top surface 54 can be transparent and optically clear. Top surface 54 can be transparent to visible light. Examples of visible light include but are not limited to X-rays, gamma rays, ultraviolet light, infrared light, radio waves and visible light.

Top surface 54 can be flat or comprise a surface area in which a portion can be flat. Such flat areas can provide an area to position a magnifying region 59 (see, FIGS. 3B, 3C). For instance, top surface 54 can comprise a magnifying region 59. Magnifying region 59 can have a magnification of 5x, 10x, 20x, 40x or 100x. In some aspects, magnifying region 59 can have a magnification of 10x or 20x. Widths, lengths and spacing of the magnifying region 59 can be controlled, in part, by the flat area of top surface 54, the overall flask size and the cell growth characteristics. The arrangement of the flat areas shown in the figures can be adjusted accordingly. In some aspects, for example, magnifying region 59 can cover a surface area of at least 5%, 10%, 20%, 30%, 40%, 50%, 60%, 70%, 80% or 90% or more of the top surface 54 of container 52.

In some aspects, cell culture flask 50 can also comprise at least one port 57. In some aspects, port 57 can serve as a vent. In some aspects, port 57 can comprise a spiral thread. In some aspects, port 57 can comprise a vent 53 (see, FIG. 3A). Cell culture flask 50 can further comprise a cap 55 (see, FIG. 3D). Cap 55 can be designed to mate with the spiral threads of port 57. In some aspects, the cell culture flask 50 can comprise at least one vent 53. In some aspects, cell culture flask 50 can have at least two vents 53. Vent 53 can be placed anywhere on container 52. In some aspects, the at least one vent 53 can be placed on one side of the center of container 52 to maximize the observation visual field (see, FIG. 3A). Port 57 can be a through-hole pass through container 52 (from the external environment to the inside of container 52). Vent 53 can extend perpendicular to the surface of container 52 of which it is placed. In some aspects, cap 55 can comprise at least one vent 53. Likewise, vent 53 can extend perpendicular to the surface of cap 55. In some aspects, the circumference of vent 53 can be between 4 mm and 8 mm. In some aspects, the circumference of vent 53 can be smaller than 4 mm or larger than 8 mm. In some aspects, cap 55 can comprise at least one vent 53. Further, vent 53 can comprise a liquid permeable gas permeable membrane. Port 57 can also comprise a liquid permeable gas permeable membrane. The liquid permeable gas permeable membrane can comprise a microporous membrane. Microporous membrane inserts are commercially available.

In some aspects, cell culture flask 50 can be sterile or sterilized.

In use, a culture medium containing cells or tissue of interest can be introduced into cell culture flask 50 through port 57. Cells, for example, can attach to an interior surface of container 52 (e.g., an interior surface opposite of bottom surface 56). Such an interior surface can be a predetermined area for culturing one or more cells. Cell culture flask 50 can be closed and warmed in an incubator. Access to the inside of container 52 can be provided by port 57 which can be covered by cap 55. The magnifying region 59 can be accessed at any time to view the cells. A larger magnifying region 59 affords a larger growing surface that can be viewed from the magnifying region 59. Generally, magnifying region 59 can be used to visualize specimens from about 2 mm. Widths, lengths and spacing of the magnifying region 59 can be controlled, in part, by the flat area requirements of the microscope, the overall flask size and the cell growth characteristics. Accordingly, the cells that can be microscopically examined will likely comprise a representative sample of the condition of all of the cells in the flask 50.

As shown in FIGS. 4A-B, cell culture plate 60 for holding and culturing one or more cells can comprise a container 62 and a lid 68. Cell culture plate 60 as a whole can have a spherical profile. Cell culture plate 60 can comprise a bottom portion 65. Bottom portion 65 of cell culture 60 can be flat so as to allow cell culture plate 60 to be positioned on a flat surface such as the stage of a microscope. Bottom portion 65 can be of any width and length. Bottom portion 65 can be relatively transparent to permit visualization of the cultured cells present in container 62.

Container 62 can comprise an internal cavity 64 and at least one vent 66. In some aspects, container 62 can comprise a plurality of vents 66. The number of vents 66 can be at least 1, 2, 3, 4, or more. One or more vents 66 can be placed anywhere on container 62. In some aspects, container 62 can have at least two vents 66. Lid 68 can comprise a top surface 69. Lid 68 can be removable and adapted to fit container 62 forming an airtight cell culture plate 60. The outer circumference of lid 68 can be less than the outer circumference of container 62. Top surface 69 of lid 68 can comprise a grip portion 63. Grip portion 63 can be of any size and at any location on lid 68. For example, grip portion 63 can extend continuously or over the entire perimeter of lid 68 or over a portion of lid 68. Grip portion 63 permits easy manual and/or automatic treatment of cell culture plate 60. Grip portion 63 facilitates opening of lid 68.

In some aspects, cell culture plate 60 can be of a sufficient optical transparency and clarity so as to permit observation during culture, such as of the color of the tissue culture medium, and of cellular characteristics (e.g., growth and morphology of cells such as by microscopy). Cell culture plate 60 can be manufactured using any stable chemical resistant transparent material. Examples of chemical resistant transparent materials include but are not limited to glass, an acrylic polymer, fluorinated ethylene propylene, ultra-high molecular weight polyethylene, polycarbonate, polystyrene or any amorphous high-performance polymer.

Cell culture plate 60 can be made of plastic material. Suitable plastic materials include but are not limited to transparent plastic materials such as polystyrene, polypropylene, polymethylpentene, polycarbonate, polymethylmethacrylate (PMMA), polymethylacrylmethylimide (PMMI) and cycloolefine (COC) copolymer, as well as of mixtures and/or copolymers of at least two of these plastic materials. In some aspects, cell culture plate 60 can be a single-use article.

Container 62 (and lid 68) can be made from an optically transparent material such as silica glass (fused quartz glass) or an optically transparent plastic. Container 62 (and lid 68) can be manufactured in one piece (integrally) or separately and then joined. In some aspects, lid 68 can comprise an optically flat transparent region where a microscope can be positioned and focused to examine one or more cells inside container 62. Similarly, as described above, bottom portion 65 of container 62 can also comprise an optically flat transparent region for placing on a microscope to examine one or more cells inside container 62.

In aspect, container 62 and/or lid 68 can made of at least one plastic material. The same or different plastic materials may be used for container 62 and lid 68. In some aspects, lid 68 and container 62 can be of the same material. In some aspects, cell culture plate 60 can be manufactured from material having both plasticity and rigidity. In some aspects, the material can be polystyrene, polycarbonate or polypropylene. Moreover, container 62 and/or lid 68 can consist of plural plastic materials. A further example for container 62 and/or lid 68 consisting of plural plastic materials is a container 62 which features a particularly transparent and/or reflection-free plastic region in at least one selected region of the container 62 and/or the lid 68. Thus, it is possible to form regions which are particularly suited for the optical observation of the cells.

In some aspects, container 62 and/or lid 68 can comprise regions made of a highly transparent plastic material like PMMA, PMMI and/or COC. In some aspects, lid 68 can be transparent in the region of the top portion 69. In some aspects, both lid 68 and container 62 can be entirely transparent. A transparent plastic material permits optical examination of cultures which are disposed in the cell culture dish without having to open the cell culture dish. For this purpose, the cell culture dish is entirely or partly made of a plastic material that can be as clear as glass.

In some aspects, internal cavity 64 can hold liquid within a space formed by container 62. The shape of the container 62 is not limited and may be circular (e.g., elliptic) or rectangular. In some aspects, container 62 can be spherical. Container 62, for example, can have the following dimensions: 35 mm by 10 mm, 60 mm by 15 mm or 100 mm by 20 mm.

In some aspects, vent 66 of container 62 can comprise a liquid permeable gas permeable membrane. The liquid permeable gas permeable membrane can comprise a microporous membrane. The membrane can be a material that can be selectively permeable to a class of molecules. Examples of useful materials include but are not limited to cellulose, polyacrylinitrile, polysulfone, polycarbonate, and polyacrilamide. Microporous membrane inserts are also commercially available.

Vent 66 can also serve as a port for introducing one or cells into the internal cavity 64 as well as to permit gaseous exchange between the internal cavity 64 and external atmosphere. Vent 66 can also permit removal of waste from internal cavity 64. In some aspects and as shown in FIGS. 4A and 4B, container 62 comprises at least one vent 66. In some aspects, container 62 can comprise a plurality of vents 66. The number of vents 66 can be at least 1, 2, 3, 4, or more. One or move vents 66 can be placed anywhere on container 62. Vent 66 can be placed on container 62 to maximize the observation visual field, to permit clear observation of the growth state of cultured cells (see, for example, FIG. 4A and FIG. 4B).

In some aspects, cell culture plate 60 can further comprise one or more slides 20, as shown in FIG. 4B. In some aspects, slide 20 can comprise a top surface 22, a bottom surface 24, at least one edge 26 and at least one projection 28 attached to said edge 26.

In some aspects, cell culture plate 60 can be sterile or sterilized.

In use, a culture medium containing cells or tissue of interest can be introduced into container 62 via internal cavity 64 or vent 66. Referring to FIG. 4B, prior to the introduction of one or more cells or tissue of interest, one or more slides 20 or 40 can be placed inside internal cavity 64. Alternatively, internal cavity 64 of container 62 can also have an interior surface for attaching one or more cells. The interior surface can be a predetermined area for culturing one or more cells. Vent 66 can also be used to replace the cell culture medium. Alternatively, a separate vent 66 can be used to remove an old culture medium. To assess the growth of the cells, for example, on slide 20, lid 68 can be removed and a user can grip projection 28 using a pair of forceps, tweezers, pincers or his/her thumb and forefinger. Cover slip 10 can then be placed over slide 20 and secured to slide 20 (forming, for example, cell culture assembly 1) by positioning the at least one projection 28 through the at least one aperture 16. Cell culture assembly 1 can be placed under a microscope for further analysis.

As shown in FIG. 5A, cell culture dish 70 can comprise a base 72 and a lid 80. Base 72 can comprise a bottom portion 74, an internal cavity 76, and a sidewall portion 78 extending upward therefrom. Base 72 can hold liquid within a space formed by the bottom portion 74 and sidewall portion 78. The shape of bottom portion 74 is not limited and may be polygonal (e.g., triangle, quadrangle), circular (e.g., elliptic) or rectangular. Base 72 can have a convex slope configuration. In some aspects, base 72 can have the following dimensions: 35 mm by 10 mm, 60 m by 15 mm or 100 mm by 200 mm. Sidewall portion 78 can be formed by surrounding bottom portion 74. Sidewall portion 78 can be inclined to bottom portion 74 at an angle from about 30° to about 60°. Sidewall portion 78 can be from about 10 mm to about 20 mm in height. In some aspects, sidewall portion 78 can be 10 mm, 15 mm or 20 mm in height. In cell culture dish 70, internal cavity 76 can be opposite to the bottom portion 74. Bottom portion 74 and sidewall portion 78 of cell culture dish 70 can form a shape similar to a conventional petri dish.

Figure 5E:
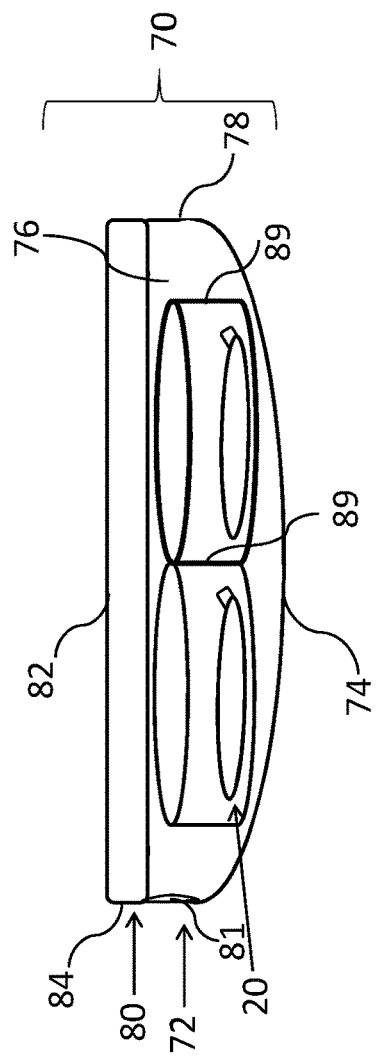
FIG. 5E is a side perspective view of an aspect of a cell culture dish according to the present disclosure.

In some aspects, base 72 can further comprise at least one vent 81, as shown in FIGS. 5C and 5E. In some aspects, base 72 can comprise a plurality of vents 81. The number of vents 81 can be at least 1, 2, 3, 4, or more. One or move vents 81 can be placed anywhere on base 72. In some aspects, base 72 can have at least two vents 81. In some aspects, the at least one vent 72 can be placed on sidewall 78. Vent 81 can extend perpendicular to the surface of sidewall 78 of which it is placed. Further, vent 78 can comprise a liquid permeable gas permeable membrane. The liquid permeable gas permeable membrane can comprise a microporous membrane. Microporous membrane inserts are commercially available.

In some aspects, cell culture dish 70 can further comprise at least one well 88. In some aspects, cell culture dish 70 can comprise two or more wells 88 defined by vertical walls 89. Referring to FIG. 5E, vertical walls 89 can be formed on the bottom portion 74 of base 72. Wells 88 can be directly provided as wells 88 on bottom portion 74 of cell culture dish 70 or formed from one or more vertical walls 89 protruding from bottom portion 74. The width of each well 88 can be sufficient for holding one or more cells. Vertical wall 89 can have a concave surface that slopes upward from lowest position to the outer edge portion of the well 88. In some aspects, each well 88 can contain a straight section, such that the path entirely or partially slopes upward linearly from the lowest position to the outer edge portion of the well 88. The straight section can suppress the movement of one or more cells as well as one or more slides 20 or 40 that can be placed into either one or more wells 88 or base 72 (without any wells) of the cell culture dish 70. Depth of each well 88 and the depth of the internal cavity 76 are not limited.

Two or more, four or more, six or more, eight or more wells 88 can be formed adjacent to each other. In some aspects, at least two wells 88 can be formed adjacent to each other and other wells 88 may be separately formed not adjacent to each other. The shape of the wells 88 is not limited and can be, for example, circular, including circular and elliptic shapes. In some aspects, well 88 can be circular, square, rectangular or other geometric shape, either similar to each other in shape or mixed in shape.

Figure 5D:
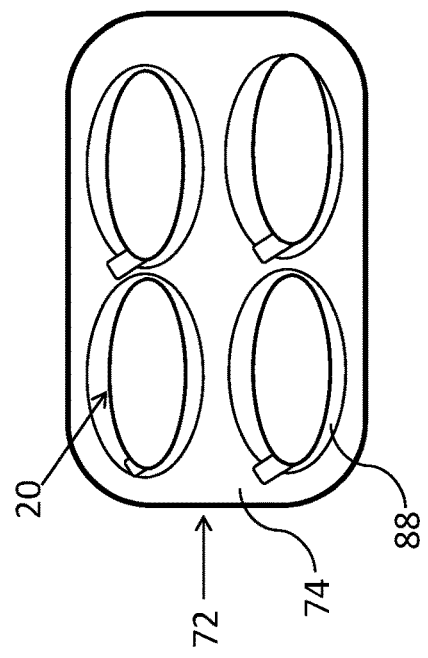
FIG. 5D is a top perspective view of an aspect of a cell culture dish according to the present disclosure.

FIG. 5C shows slide 20 in internal cavity 76 of base 72. In some aspects, slide 20 can be placed in internal cavity 76 of base 72 in which no wells 88 are present. In some aspects, internal cavity 76 of cell culture dish 70 can comprise a plurality of wells 88, wherein all of the wells 88 have common (interior) vertical walls 89. In some aspects, two, three, four, five, six or more wells 88 can be juxtaposed side by side having common (interior) vertical walls 89. For example, FIGS. 5D and 5E show examples of two or more wells 88 positioned in the internal cavity 76 of cell culture dish 70. Further, FIGS. 5D and 5E show slide 20 placed inside two or more wells 88 in the internal cavity 76 of cell culture dish 70, respectively.

Lid 80 can comprise a top portion 82 and a wall portion 84 that extends downward therefrom. Lid 80 can be adapted to cover base 72. FIGS. 5A and 5C show cell culture dish 70 in a fully closed position. For this, wall portion 84 of lid 80 can be in contact with sidewall portion 78 of base 72. The user can close or place cell culture dish 70 in a sealing position by pushing lid 80 down on base 72. For this, a single hand or finger is needed. The risk of contamination of one or more cells when arranging lid 80 on base 72 can be reduced. Leak of cell culture medium and excess movement of the cells can be avoided when cell culture dish 70 is in the sealing position. Risk of exposure to contaminated medium by the user can also be reduced.

In some aspects, sidewall 78 can further comprise at least one vent 81, as shown in FIGS. 5C and 5E. In some aspects, sidewall 78 can comprise a plurality of vents 81. The number of vents 81 can be at least 1, 2, 3, 4, or more. One or move vents 81 can be placed anywhere on sidewall 78. In some aspects, sidewall 78 can have at least two vents 81. In some aspects, the at least one vent 81 can be placed on one side of the center of sidewall 78. Vent 81 can extend perpendicular to the surface of sidewall 78 of which it is placed. Further, vent 81 can comprise a liquid permeable gas permeable membrane. The liquid permeable gas permeable membrane can comprise a microporous membrane. Microporous membrane inserts are commercially available.

Referring to FIG. 5B, top portion 82 of lid 80 can comprise a magnifying region 86. Magnifying region 86 can be formed of a transparent material. The transparent material can be plastic or glass. Magnifying region 86 can be any shape or configuration, and can be optically clear and transparent to visible light. Examples of visible light include but are not limited to X-rays, gamma rays, ultraviolet light, infrared light, radio waves and visible light. Magnifying region 86 can be used in place of a microscope, i.e., to examine one or more cells inside cell culture dish 70. Widths, lengths and spacing of the magnifying region 86 on lid 80 can be controlled, in part, by the overall lid 80 size. Magnifying region 86 can make up part of or be continuous with the top portion 82 of lid 80. Generally, magnifying region 86 can be about 10× or 20×. In some aspects, magnifying region 86 can have a magnification of 10×, 20× or 40×. Magnifying region 86 permits optical examination of cultures which are disposed in the cell culture dish 70 without having to open the cell culture dish 70 or transport the cell culture dish 70 to a microscope.

Cell culture dish 70 can be manufactured using any stable chemical resistant transparent material. Examples of chemical resistant transparent materials include but are not limited to glass, an acrylic polymer, fluorinated ethylene propylene, ultra-high molecular weight polyethylene, polycarbonate, polystyrene or any amorphous high-performance polymer.

Cell culture dish 70 can be made of plastic material. Suitable plastic materials include but are not limited to transparent plastic materials such as polystyrene (PS), polypropylene (PP), polymethylpentene, polycarbonate (PC), polymethylmethacrylate (PMMA), polymethylacrylmethylimide (PMMI) and cycloolefine copolymer (COC), as well as of mixtures and/or copolymers of at least two of these plastic materials. In some aspects, cell culture dish 70 can be a single-use article. In some aspects, cell culture dish 70 can be sterilized prior to use. In some aspects, base 72 can be sterilized prior to use.

Base 72 (and lid 80) can be made from an optically transparent material such as silica glass (fused quartz glass) or an optically transparent plastic. Base 72 (and lid 80) can be manufactured in one piece (integrally) or separately and then joined.

In some aspects, base 72 and/or lid 80 can made of at least one plastic material. The same or different plastic materials may be used for base 72 and lid 80. In some aspects, lid 80 and base 72 can be of the same material. In some aspects, the material can be polystyrene. Moreover, base 72 and/or lid 80 can consist of plural plastic materials. A further example for base 72 and/or lid 80 consisting of plural plastic materials is a base 72 which features a particularly transparent and/or reflection-free plastic region in at least one selected region of the base 72 and/or the lid 80. Thus, it is possible to form regions which are particularly suited for the optical observation of the cells.

In some aspects, base 72 and/or lid 80 can comprise regions made of a highly transparent plastic material like PMMA, PMMI and/or COC. In some aspects, lid 80 and base 72 can be transparent in the region of the top portion 82 and bottom portion 74, respectively. In some aspects, both lid 80 and base 72 can be entirely transparent. A transparent plastic material permits optical examination of cultures which are disposed in the cell culture dish without having to open the cell culture dish. For this purpose, the cell culture dish can be entirely or partly made of a plastic material that can be as clear as glass.

In some aspects, cell culture dish 70 can be sterile or sterilized.

In use, a culture medium containing cells or tissue of interest can be introduced into base 72 via internal cavity 76 by removing lid 80. Referring to FIG. 5C, prior to the introduction of a culture medium, one or more slides 20 or 40 can be placed inside internal cavity 76. Alternatively, internal cavity 76 of base 72 can also have an interior surface for attaching one or more cells. The interior surface can be a predetermined area for culturing one or more cells. Further, bottom portion 74 can be configured to comprise two or more wells 88 for accommodating growth medium and one or more cells. In some aspects, prior to the introduction of a culture medium, one or more slides 20 can be placed inside one or more wells 88 positioned in cell culture dish 70 (see, FIGS. 5D and 5E). It is an aspect of this disclosure, that cell culture dish 70 be a modular system, such that any wells 88 that are a part of cell culture dish 70 that are not needed or used can be easily removed. Lid 80 can be placed over base 72 so that cell culture dish 70 can be in a closed position, as shown in FIG. 5E. Once cell culture dish 70 is in the closed position, it can be placed in an incubator; and magnifying region 86 can be accessed at any time to view the cells. A larger magnifying region 86 affords a larger growing surface that can be viewed from the magnifying region 86. Widths, lengths and spacing of the magnifying region 86 can be controlled, in part, by the flat area requirements of the microscope, the overall dish 70 size and the cell growth characteristics. Accordingly, the cells that can be microscopically examined will likely comprise a representative sample of the condition of all of the cells in the cell culture dish 70.

Figure 7:
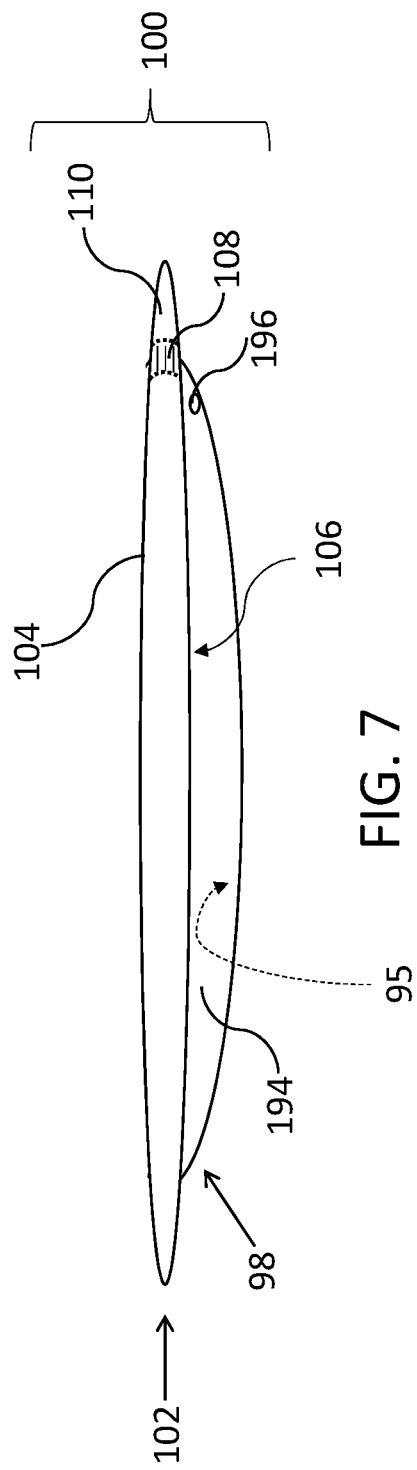
FIG. 7 is a side perspective view of an aspect of a cell culture assembly according to the present disclosure.

Disclosed herein, with reference to FIGS. 6-7, cell culture assemblies 90 and 100 useful for holding and culturing one or more cells are illustrated. Cell culture assemblies 90 and 100 improve the means for growing and assessing the dynamic physiologic interactions between different cell types in general and in disease under a variety of conditions. For instance, secreted factors or direct contact of adherent or suspended cells with the outer layers that elicit functional effects including but not limited to cellular and morphologic changes and activation or inhibition of signaling pathways can be assessed. As described herein, cell culture assembly 90 permits the growth and assessment of one or more cells of interest in direct or indirect contact with at least two different cell populations (see, FIG. 6). Alternatively, cell culture assembly 100 permits the growth and assessment of one or more cells of interest in direct or indirect contact with at least one different cell population (see, FIG. 7). Further, one or more slides 20 and 40 (or 120) can be placed in bottom chamber 98 for further analysis (see, FIG. 6B).

As shown in FIG. 6, cell culture assembly 90 comprises a top chamber 92, a bottom chamber 98 and a semipermeable vessel 102. In general and as a whole, cell culture assembly 90 can have a cylindrical or spherical profile but any shape is within the scope of this disclosure. Top and bottom chambers 92 and 98 can be made of a plastic having both plasticity and rigidity such as polycarbonate, polystyrene or polypropylene. They can be made by injection molding. Top and bottom chambers 92 and 98 can also be made of glass material. Top and bottom chambers 92 and 98 can hold a cell culture medium and one or more cells or only a cell culture medium. The inside bottom surface 95 of the bottom chambers 98 can be subjected to surface treatment such as hydrophilicity imparting surface treatment for securing cell adhesion performance, which can allow culture and growth of adhesive cells and the like. In some aspects, top chamber 92 can comprise an internal cavity 94 and a port 96. In some aspects, bottom chamber 98 can comprise an internal cavity 194 and a port 196. Ports 96 and 196 can serve to introduce a culture medium or cells into an internal cavity 94 and 194 of top and/or bottom chambers 92 and 98, respectively, as well as remove waste from the internal cavity 94 and 194. Ports 96 and 196 can also serve as a vent permitting gaseous exchange between internal cavity 94 and 194 and the external atmosphere. In some aspects, ports 96 and 196 can comprise a liquid permeable gas permeable membrane. The liquid permeable gas permeable membrane can comprise a microporous membrane. The membrane can be a material that can be selectively permeable to a class of molecules. Examples of useful materials include but are not limited to cellulose, polyacrylinitrile, polysulfone, polycarbonate, and polyacrilamide. Microporous membrane inserts are also commercially available. In some aspects, ports 96 and 196 can be fitted with a cap 110 to prevent exchange with the external atmosphere.

Semi-permeable vessel 102 can also comprise port 108. Port 108 can serve as an entry point of one or more cells, proteins, factors, therapeutics, or other material. Port 108 can comprise a spiral thread. Port 108 can be positioned at one end of the semi-permeable vessel 102. Cap 110 can be designed to mate with spiral threads of port 108 of semi-permeable vessel 102. In some aspects, semi-permeable vessel 102 can be positioned between top chamber 92 and bottom chamber 98. Semi-permeable vessel 102 can also be configured to fluidly interconnect top chamber 92 and bottom chamber 98. In some aspects, semi-permeable vessel 102 can comprise top and bottom membranes 104 and 106. Top and bottom 104 and 106 membranes can have a specific porosity. Such porosity can allow the passage of, for example, cellular expression products through the membrane and to prevent passage of cells through the membrane.

Top and bottom membranes 104 and 106 can be made from material that is coated with desired macromolecules. Further, top and bottom membranes 104 and 106 can serve as a filter or sieve, thus permitting a select size or range of molecules to enter the culture medium. The pore size of top and bottom membranes 104 and 106 can range from about 0.2 μm to 0.4 μm.

In use, a culture medium containing cells or tissue of interest can be introduced into top chamber 92 and/or bottom chamber 98 through the corresponding ports 96 and 196. Referring to FIG. 6B, prior to introduction of a culture medium, one or more slides 20 or 40 (or 120) can be placed inside internal cavity 194 of bottom chamber 98. Alternatively, internal cavity 194 of bottom chamber 98 can also have an inside bottom surface 95 for attaching one or more cells. The inside bottom surface 95 can be a predetermined area for culturing one or more cells. Media-containing cells can also be introduced into semi-permeable vessel 102. In living systems, cells within a specific tissue do not exist in isolation. For example, vascular cells often include endothelial cells, vascular smooth muscle cells, pericytes, and fibroblasts. Additionally, cellular systems often recruit immune cells including macrophages. These different types of cells may play similar or distinct roles in response to various triggers. Thus, cell culture assembly 90 can be used to evaluate an in vivo system such as cell-to-cell contact that permits dynamic interactions and exchanges of materials between different cell types in an in vitro set up. Cell culture assembly 90 can be used to mimic and assess interactions between multiple cell types in an integrated manner. For example, the effects of epithelial cancer cells on surrounding vascular tissues can be analyzed by taking into consideration the dynamic interplay between the different cell types.

More specifically, media-containing cells (e.g., cancer cells) can be introduced into semi-permeable vessel 102 of cell culture assembly 90 through port 96 and/or port 196. In some aspects, media-containing cells can almost completely filling semi-permeable vessel 102. Semi-permeable membrane vessel 102 allows bidirectional exchange of secretions between the same or different cells (e.g., one or more of a vascular type cell) present in top chamber 92 and bottom chamber 98, while preventing exchange of solid materials, such as cells or cell debris, due to the presence of a top membrane 104 and a bottom membrane 106. For example, epithelial cancer cells may be placed in semi-permeable vessel 102, while endothelial cells and smooth muscle cells can be placed in the top chamber 92 and bottom chamber 98, respectively, (cell types can be chosen and placed in any chamber based on specific experimental design). Top chamber 92 and bottom chamber 98 can be filled almost completely with media containing-cells. Various treatments, such as growth factor stimulation or receptor inhibition against the cancer cells in semi-permeable vessel 102 can be simultaneously analyzed for response of the vascular cells present in top chamber 92 and bottom chamber 98, respectively.

At the end of experiment, culture media can be removed from the top chamber 92, bottom chamber 98 and semi-permeable vessel 102 and replaced with cold Phosphate Buffer Saline (PBS) using the corresponding ports 96 and 196. After rinsing and removal of cold PBS, cells in bottom chamber 98 can be lysed and collected. Next, cell culture assembly 90 can be turned 180-degrees, so that top chamber 92 can be located on the bottom of cell culture assembly 90, and the same procedure can repeated by lysing the cells and collecting the lysed cells from top chamber 92. Lastly, semi-permeable vessel 102 can be removed or separated from cell culture assembly 90 and placed in an accompanying sterile cell collection vessel. The cell collection vessel is separate from the semi-permeable vessel 102 of the present disclosure. The cold PBS can be removed from semi-permeable vessel 102, replaced with lysis reagent and cells collected. Cell culture assembly 90 can be used for the evaluation of holding of many different cell types based on experimental design.

As shown in FIG. 7, cell culture assembly 100 comprises a chamber 98 and a semi-permeable vessel 102. In general and as a whole, cell culture assembly 100 can have a cylindrical or spherical profile but any shape is within the scope of this disclosure. Chamber 98 can be made of aplastic having both plasticity and rigidity such as polycarbonate, polystyrene or polypropylene. They can be made by injection molding. Chamber 98 can also be made of glass material. Chamber 98 can hold a cell culture medium and one or more cells or only a cell culture medium. The inside bottom surface 95 of chamber 98 can be subjected to surface treatment such as hydrophilicity imparting surface treatment for securing cell adhesion performance, which can allow culture and growth of adhesive cells and the like. In some aspects, chamber 98 can comprise an internal cavity 194 and a port 196. Port 196 can serve to introduce a culture medium or cells into an internal cavity 194 of chamber 98 as well as remove waste from the internal cavity 194. Port 196 can also serve as a vent permitting gaseous exchange between internal cavity 194 and the external atmosphere. In some aspects, port 196 can comprise a liquid permeable gas permeable membrane. The liquid permeable gas permeable membrane can comprise a microporous membrane. The membrane can be a material that can be selectively permeable to a class of molecules. Examples of useful materials include but are not limited to cellulose, polyacrylinitrile, polysulfone, polycarbonate, and polyacrilamide. Microporous membrane inserts are also commercially available. In some aspects, port 196 can be fitted with a cap 110 (or plug) to prevent exchange with the external atmosphere.

Semi-permeable vessel 102 can also comprise port 108. Port 108 can serve as an entry point of one or more cells, proteins, factors, therapeutics, or other material. Port 108 can comprise a spiral thread. Port 108 can be positioned at one end of the semi-permeable vessel 102. Cap 110 can be designed to mate with spiral threads of port 108 of semi-permeable vessel 102. In some aspects, semi-permeable vessel 102 can be positioned above or adjacent to chamber 98. Semi-permeable vessel 102 can also be configured to fluidly interconnect to chamber 98. In some aspects, semi-permeable vessel 102 can comprise top and bottom membranes 104 and 106. Top and bottom 104 and 106 membranes can have a specific porosity. Such porosity can allow the passage of, for example, cellular expression products through the membrane and to prevent passage of cells through the membrane.

Top and bottom membranes 104 and 106 can be made from material that is coated with desired macromolecules. Further, top and bottom membranes 104 and 106 can serve as a filter or sieve, thus permitting a select size or range of molecules to enter the culture medium. The pore size of top and bottom membranes 104 and 106 can range from about 0.2 µm to 0.4 µm.

In use, a culture medium containing cells or tissue of interest can be introduced chamber 98 through the corresponding port 108. Prior to introduction of a culture medium, one or more slides 20 or 40 (or 120) can be placed inside internal cavity 194 of chamber 98. Alternatively, internal cavity 194 of chamber 98 can also have an inside bottom surface 95 for attaching one or more cells. The inside bottom surface 95 can be a predetermined area for culturing one or more cells. Similar to cell culture assembly 90, cell culture assembly 100 can be used to evaluate an in vivo system such as cell-to-cell contact that permits dynamic interactions and exchanges of materials between different cell types in an in vitro set up. Cell culture assembly 100 can be used to mimic and assess interactions between multiple cell types in an integrated manner. For example, the effects of epithelial cancer cells on surrounding vascular tissues can be analyzed by taking into consideration the dynamic interplay between the different cell types.

More specifically, media-containing cells (e.g., cancer cells) can be introduced to semi-permeable vessel 102 of cell culture assembly 100 by removing lid 110 and almost completely filling semi-permeable vessel 102 via port 108, followed by securing cap 110 to port 108. Semi-permeable membrane vessel 102 allows the secretions of cells present in semi-permeable vessel 102 and chamber 98, while preventing exchange of solid materials, such as cells or cell debris, due to the presence of bottom membrane 106. For example, epithelial cancer cells may be placed in semi-permeable vessel 102, while a different cell type (e.g., endothelial cells or vascular smooth muscle cells) can be placed in chamber 98 (cell types can be chosen and placed in any chamber based on specific experimental design). Chamber 98 can be filled almost completely with media containing-cells. Various treatments, such as growth factor stimulation or receptor inhibition against the cancer cells in semi-permeable vessel 102 can be simultaneously analyzed for response of the cells present chamber 98.

The article of manufacture can further include, for example, packaging materials, instructions for use (e.g., written or visual materials). The cell culture assemblies, flask, plates, and dishes and their individual components can also include a legend (e.g., a printed label or insert or other medium describing the product's use (e.g., an audio- or videotape)). The legend can be associated with the container or packaging (e.g., affixed to the container or packaging) and can describe the manner in which the components of the various assembles or systems can be used either together or individually.

A number of embodiments of the present disclosure have been described. Nevertheless, it will be understood that various modifications can be made without departing from the spirit and scope of the disclosure. Accordingly, other embodiments are within the scope of the following claims.

What is claimed is:

1. A cell culture assembly for holding one or more cells, the assembly comprising:
    a slide comprising:
        a top surface;
        a bottom surface;
        at least one edge; and
        at least one projection attached to said edge; and
    a cover slip comprising:
        a top surface;
        a bottom surface; and
        at least one aperture extending from the top surface to the bottom surface of the cover slip, wherein each aperture of the at least one aperture is configured to receive a respective projection of said at least one projection;
    wherein said cover slip overlaps and is in communication with at least a portion of said slide when the at least one aperture accommodates the at least one projection, wherein a first projection of the at least one projection extends through a first aperture of the at least one aperture of the coverslip; wherein said cover slip comprises an adhesive on said bottom surface capable of bonding said top surface of said slide to said cover slip; and
    wherein said cover slip is transparent.

2. The cell culture assembly of claim 1, wherein said cover slip further comprises a labeling region.

3. The cell culture assembly of claim 1, wherein said cover slip is transparent to visible light.

4. The cell culture assembly of claim 1, wherein said slide is sterile.

5. The cell culture assembly of claim 1, wherein said at least one projection is self-locking in said aperture.

6. The cell culture assembly of claim 1, wherein the slide has a smaller perimeter, circumference or area compared to the cover slip.

* * * * *